US00PP14031P29

(12) United States Plant Patent
Takeshita et al.

(10) Patent No.: US PP14,031 P2
(45) Date of Patent: Jul. 29, 2003

(54) CALIBRACHOA PLANT NAMED 'ILLUMINATION CHERRY PINK'

(75) Inventors: Daigaku Takeshita, Utsunomiya (JP); Tsutomu Tokita, Omiya (JP); Saori Watanabe, Ujiie-machi (JP); Noboru Onishi, Thousand Oaks, CA (US); Kunihiro Hayashida, Utsunomiya (JP)

(73) Assignees: Kirin Brewery Co., Ltd., Tokyo (JP); Tokita Seed Co., Ltd., Saitama-Ken (JP)

( * ) Notice: Subject to any disclaimer, the term of this patent is extended or adjusted under 35 U.S.C. 154(b) by 0 days.

(21) Appl. No.: 10/094,320

(22) Filed: Mar. 8, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—June Hwu
(74) *Attorney, Agent, or Firm*—C. A. Whealy

(57) ABSTRACT

A distinct cultivar of Calibrachoa plant named 'Illumination Cherry Pink', characterized by its cascading and prostrate plant habit; freely branching growth habit; early flowering habit; red purple-colored flowers with yellow-colored throat; and good weather tolerance.

2 Drawing Sheets

BOTANICAL CLASSIFICATION/CULTIVAR DESIGNATION

Calibrachoa sp. cultivar Illumination Cherry Pink.

BACKGROUND OF THE INVENTION

The present Invention relates to a new and distinct cultivar of Calibrachoa plant, botanically known as Calibrachoa sp., and hereinafter referred to by the name 'Illumination Cherry Pink'.

The new Calibrachoa is a product of a planned breeding program conducted by the Inventors in Tochigi, Japan. The objective of the breeding program is to create new early flowering Calibrachoa cultivars that have stronger growth and attractive flower coloration.

The new Calibrachoa originated from a self-pollination made by the Inventors in April, 1997, in Tochigi, Japan, of an unnamed proprietary Calibrachoa seedling selection, not patented. The new Calibrachoa was discovered and selected by the Inventors as a single flowering plant within the progeny of the stated self-pollination grown in a controlled environment in Tochigi, Japan, in July, 1998. The selection of this plant was based on its strong plant growth habit and attractive flower coloration.

Asexual reproduction of the new cultivar by terminal cuttings taken in a controlled environment in Saitama-ken, Japan, since January, 1999, has shown that the unique features of this new Calibrachoa are stable and reproduced true to type in successive generations.

SUMMARY OF THE INVENTION

Plants of the cultivar Illumination Cherry Pink have not been observed under all possible environmental conditions. The phenotype may vary somewhat with variations in environment such as temperature and light intensity without, however, any variance in genotype.

The following traits have been repeatedly observed and are determined to be the unique characteristics of 'Illumination Cherry Pink'. These characteristics in combination distinguish 'Illumination Cherry Pink' as a new and distinct cultivar of Calibrachoa:

1. Cascading and prostrate plant habit.
2. Freely branching growth habit.
3. Early flowering habit.
4. Red purple-colored flowers with yellow-colored throat.
5. Good weather tolerance; tolerant to wind, rain, and low and high temperatures.

Plants of the new Calibrachoa can be compared to plants of the parent, the unnamed proprietary Calibrachoa selection. In side-by-side comparisons conducted by the Inventors in Tochigi, Japan, plants of the new Calibrachoa differed from plants of the parent primarily in growth habit as plants of the new Calibrachoa were more prostrate and not as upright as plants of the parent. In addition, plants of the new Calibrachoa had smaller flowers than plants of the parent.

Plants of the new cultivar can also be compared to plants of the cultivar Sunbelkupi, disclosed in U.S. Plant Pat. No. 10,287. In side-by-side comparisons conducted by the Inventors in Tochigi, Japan, plants of the new Calibrachoa differed from plants of the cultivar Sunbelkupi in the following characteristics:

1. Plants of the new Calibrachoa had darker green-colored leaves than plants of the cultivar Sunbelkupi.
2. Plants of the new Calibrachoa had slightly smaller flowers than plants of the cultivar Sunbelkupi.
3. Plants of the new Calibrachoa and the cultivar Sunbelkupi differed in corolla coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photograph may differ slightly from the color values cited in the detailed botanical description which accurately describe the colors of the new Calibrachoa.

The photograph on the first sheet comprises a side perspective view of a typical flowering plant of 'Illumination Cherry Pink'.

The photograph on the second sheet comprises a close-up view of a typical flower of 'Illumination Cherry Pink'.

DETAILED BOTANICAL DESCRIPTION

In the following description, color references are made to The Royal Horticultural Society Colour Chart except where general terms of ordinary dictionary significance are used. Twenty-centimeter containers with three plants per container were used for the aforementioned photographs and the following description. Plants were grown under conditions which closely approximate commercial production conditions during the winter in Santa Paula, Calif. in a polyethylene-covered greenhouse. Plants used for the photographs and the description were about 14 weeks from planting rooted young plants. During the production period, day temperatures averaged 28° C., night temperatures averaged 21° C., and light levels were about 5,000 footcandles.

Botanical classification: Calibrachoa sp. cultivar Illumination Cherry Pink.

Parentage: Self-pollination of an unnamed proprietary selection of Calibrachoa sp., not patented.

Propagation:

*Type cutting.*—Terminal vegetative cuttings.

*Time to initiate roots.*—Summer: About 3 days at 25° C. Winter: About 7 days at 20° C.

*Time to produce a rooted young plant.*—Summer: About 21 days at 25° C. Winter: About 23 days at 22° C.

*Root description.*—Fine, fibrous, and white in color.

*Rooting habit.*—Freely branching; dense.

Plant description:

*Form.*—Annual flowering plant; cascading and prostrate plant habit; low mounded; short internodes, dense and bushy appearance.

*Plant height* (*from soil level to top of plant plane*).—About 18 cm.

*Plant diameter* (*area of spread*).—About 80 cm.

*Growth rate.*—Relatively rapid.

*Branching habit.*—Freely basal branching, about 6 to 8 basal branches per plant; lateral branches develop at potentially every node; pinching is typically not required.

*Lateral branch description.*—Length: About 45 cm. Diameter: About 3 mm. Internode length: About 5 to 10 mm. Orientation: Initially upright, then horizontal. Texture: Pubescent; short, fine hairs. Strength: Strong, but flexible. Color: 144A.

*Foliage description.*—Leaves simple, generally symmetrical. Arrangement: Alternate before flowering, then opposite. Length: About 3 cm. Width: About 1 cm. Shape: Narrowly elliptic. Apex: Broadly acute. Base: Acute. Margin: Entire. Texture, upper surface: Coarse; slightly glandular; slightly pubescent. Texture, lower surface: Coarse; slightly glandular; glabrous. Venation pattern: Pinnate; arcuate. Color: Young and fully expanded foliage, upper surface: 147A. Young and fully expanded foliage, lower surface: 147B. Venation, upper surface: 147B. Venation, lower surface: 147C. Petiole length: About 5 mm. Petiole diameter: About 1 mm. Petiole color: 144B.

Flower description:

*Flower type and habit.*—Flowers face upright or outward; solitary and axillary; salverform. Freely flowering habit, about 20 to 22 flowers and flower buds per lateral stem. Flowers persistent. Flowers not fragrant.

*Natural flowering season.*—Spring until frost in the autumn; flowering continuous during this period.

*Time to flower.*—Early flowering; plants begin flowering about 2 weeks after planting.

*Flower longevity on the plant.*—About 2 weeks.

*Flower size.*—Diameter: About 3.9 cm. Tube length: About 2.8 cm.

*Flower buds* (*showing color*).—Length: About 2 cm. Diameter: At apex, about 5 mm; at base, about 3 mm. Shape: Roughly oblong. Color: 79C.

*Corolla.*—Arrangement/appearance: Single whorl of five petals, fused into flared trumpet. Petal length from throat: About 1.5 cm. Petal width: About 1.4 cm. Petal shape: Spatulate to flabellate. Petal apex: Rounded. Petal margin: Entire. Petal texture: Smooth, glabrous; velvety. Color: Petal, when opening, upper surface: Brighter than 60A; venation, close to 60A. Petal, when opening, lower surface: 61B; venation, closer to 61B. Petal, opened flower, upper surface: Darker than 57A and brighter than 63A; venation, close to 57A to 60A to 63A; color does not fade with subsequent development. Petal, opened flower, lower surface: 61B to 61C; venation, close to 61B to 61C. Flower throat (inside): 14A; venation, close to 14A. Flower tube (outside): 145D; venation, close to 145D.

*Sepals.*—Arrangement/appearance: Single whorl of five sepals fused at base; star-shaped. Length: About 1.5 cm. Width: About 2 mm. Shape: Narrowly elliptic. Apex: Acute. Margin: Entire. Texture, upper and lower surfaces: Smooth, glabrous. Color: Young and fully expanded sepals, upper and lower surfaces: 146A.

*Peduncles.*—Length: About 2.2 cm. Width: About 1 mm. Strength: Moderately strong. Angle: About 45° from stem. Texture: Pubescent. Color: 144A.

*Reproductive organs.*—Stamens: Quantity: Five per flower. Anther shape: Oval. Anther length: Less than 1 mm. Anther color: 10A. Pollen amount: Scarce. Pollen color: 7A. Pistils: Quantity: One per flower. Pistil length: About 1.5 cm. Stigma shape: Anvil-shaped; curved. Stigma color: 144A. Style length: About 1.2 cm. Style color: 144C. Ovary color: 150C.

*Seed/fruit.*—Seed and fruit production has not been observed.

Disease/pest resistance: Plants of the new Calibrachoa have not been noted to be resistant to pathogens and pests common to Calibrachoa.

Weather/temperature tolerance: Plants of the new Calibrachoa are tolerant to rain and wind and have been observed to tolerate temperatures from 3 to 35° C.

It is claimed:

1. A new and distinct cultivar of Calibrachoa plant named 'Illumination Cherry Pink', as illustrated and described.

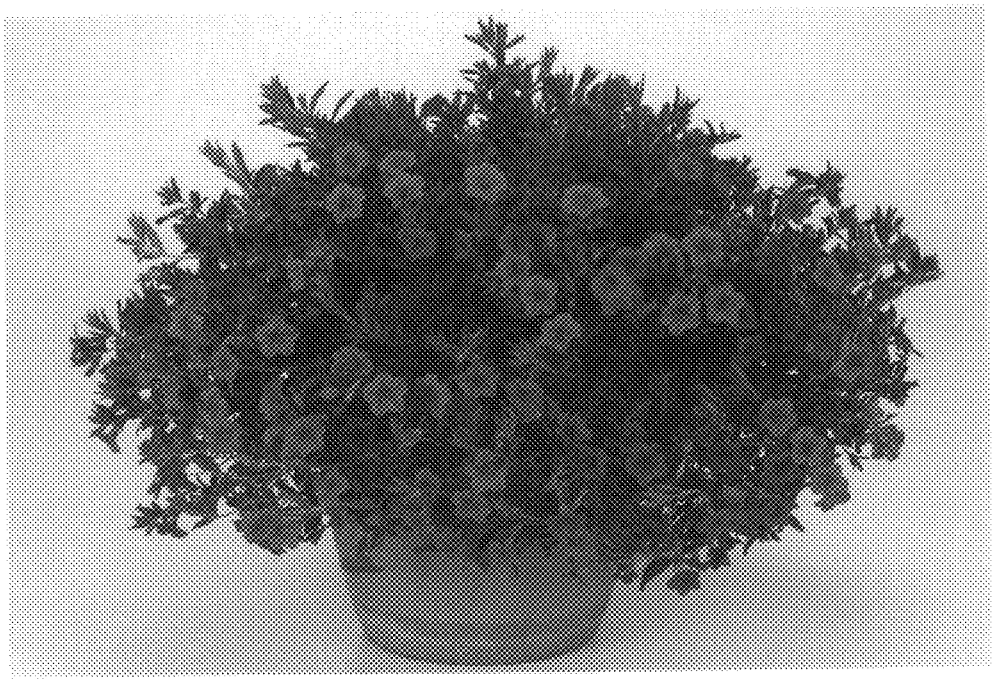

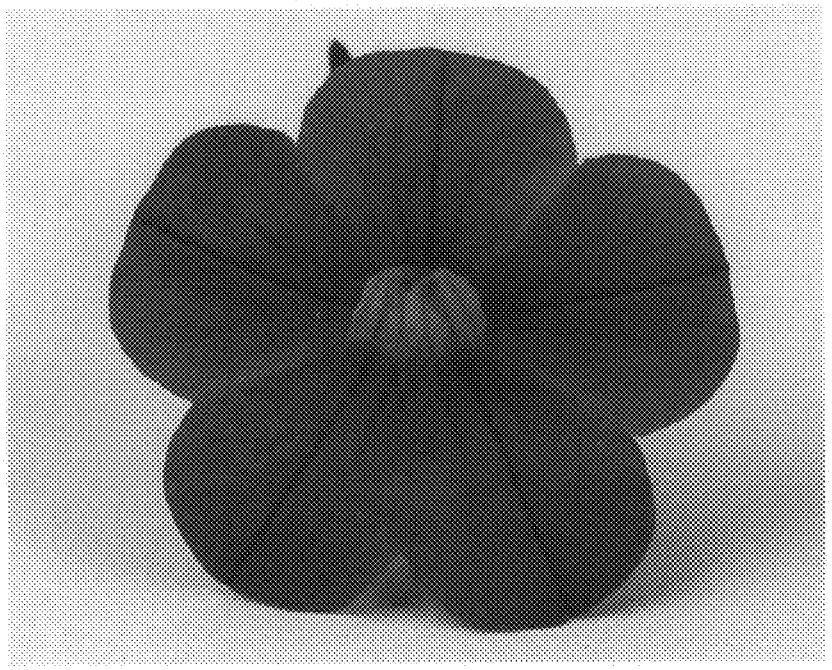

* * * * *